United States Patent [19]

Matsui et al.

[11] 4,438,041

[45] Mar. 20, 1984

[54] PROCESS FOR PREPARING ESTERS OF CYANOACETIC ACIDS

[75] Inventors: Kanenobu Matsui; Shinichiro Uchiumi; Mitsuo Takahashi; Hideki Asada; Masaru Kurahashi, all of Ube, Japan

[73] Assignee: UBE Industries, Ltd., Tokyo, Japan

[21] Appl. No.: 384,417

[22] Filed: Jun. 2, 1982

[30] Foreign Application Priority Data

Jun. 9, 1981 [JP] Japan .................................. 56-87471

[51] Int. Cl.$^3$ .................. C07C 120/00; C07C 121/16; C07C 121/46; C07C 121/66
[52] U.S. Cl. .............................. 260/464; 260/465 D; 260/465.4; 260/404
[58] Field of Search ................ 260/465.4, 465 D, 464

[56] References Cited

U.S. PATENT DOCUMENTS 4,097,517  1/1978  Rogic et al. ...................... 260/465.4

OTHER PUBLICATIONS

"The Chemistry of Carboxylic Acids and Esters," Cordes, [Patai, Editor] (1969), pp. 643–644, *Interscience Publishers.*

*Primary Examiner*—Joseph Paul Brust
*Attorney, Agent, or Firm*—Frishauf, Holtz, Goodman & Woodward

[57] ABSTRACT

A novel process for preparing an ester of cyanoacetic acid which comprises reacting a cyanoacetaldehyde acetal, hydroxylamine and an alcohol.

9 Claims, No Drawings

PROCESS FOR PREPARING ESTERS OF CYANOACETIC ACIDS

This invention relates to a novel process for preparing an ester of cyanoacetic acid.

Esters of cyanoacetic acids have various uses as starting materials for pharmaceuticals, agricultural chemicals, perfumes, etc.

Conventionally, an ester of cyanoacetic acid has been prepared by reacting monochloroacetic acid with sodium cyanide, followed by the esterification of the thus obtained cyanoacetic acid.

However, the prior art process has industrially serious problems in that prudent care must be taken in the reaction operation, the treatment of the waste liquor requires special apparatuses and so forth, due to the use of toxic sodium cyanide.

The present inventors have made extensive studies to establish an industrially advantageous process for preparing an ester of cyanoacetic acid. As the result, the present inventors have found that difficulties in the conventional process were overcome and an ester of cyanoacetic acid can be prepared industrially with advantage by subjecting a cyanoacetaldehyde acetal, hydroxylamine and an alcohol to reaction with each other.

Namely, this invention provides a process for preparing an ester of cyanoacetic acid by a novel reaction, which has many advantages in that the reaction operation and the treatment of the waste liquor may simply be carried out, and the process does not require any special reaction apparatus, because of the higher safety of the starting material as compared with those of the conventional process.

The cyanoacetaldehyde acetal which is a starting material in this invention is represented by the general formula:

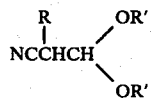

wherein R represents a hydrogen atom, an alkyl group, a cycloalkyl group, a phenyl group, an aralkyl group, and R' represents an alkyl group, a cycloalkyl group, a phenyl group, an aralkyl group or both R's represent alkylene groups to form a ring by linking with each other.

The hydrogen atom or atoms of the alkyl group, the cycloalkyl group, the phenyl group or the aralkyl group represented by R and R' may be replaced with such a substituent as a halogen atom, a nitro group or the like.

As the alkyl group represented by R and R', there may be mentioned, for example, methyl, ethyl, propyl, butyl, pentyl, hexyl, heptyl, octyl, etc.

As the cycloalkyl group represented by R and R', there may be mentioned, for example, cyclopentyl, cyclohexyl, cycloheptyl and substituted cycloalkyl groups such as 2-chlorocyclohexyl, 4-nitrocyclohexyl, etc. As the aralkyl group represented by R and R', there may be mentioned, for example, benzyl, β-phenylethyl, and substituted aralkyl groups such as o-chlorobenzyl, m-chlorobenzyl, p-nitrobenzyl, etc.

These cyanoacetaldehyde acetals (described above) which are known compounds can readily be synthesized, for example, by subjecting an acrylonitrile and an alcohol to catalytic reaction in the presence of a platinum group metal series catalyst.

Hydroxylamine may be used as such or in a form of salt such as sulfate, chloride, phosphate, acetate, etc. Moreover, an aqueous solution of hydroxylamine sulfate obtainable in the process for lactam synthesis, that is to say, an aqueous solution of hydroxylamine sulfate which has been obtained by absorbing sulfur dioxide in an aqueous solution of ammonium nitrite and ammonia, and hydrolyzing the so obtained hydroxylamine ammonium disulfate and which contains sulfuric acid, ammonium sulfate and so on, may also be employed as such.

Hydroxylamine (a salt thereof as well) may be used in an amount of 0.1 to 10 moles, preferably, 1 to 5 moles, per one mole of a cyanoacetaldehyde acetal.

As the alcohol are useful an aliphatic alcohol such as methanol, ethanol, n(or i)-propanol, n(i, sec, tert-)butanol, amyl alcohol, hexanol and octanol; an alicyclic alcohol such as cyclohexanol and methylcyclohexanol; and so on. These alcohols may contain therein a substituent such as, for example, a nitro group or a halogen atom which does not inhibit the reaction.

Since these alcohols function as a solvent as well, it usually is preferred to use them in large excess of the other starting materials.

Further, the reaction may also be carried out in such a solvent as an ester, an ether, nitrobenzene, dimethylsulfone and N,N-dimethylformamide, besides the alcohol.

In this invention, the rate of the reaction can be accelerated and the yield of the desired product can be enhanced by adding a proper amount of an acid such as sulfuric acid, hydrochloric acid, phosphoric acid, sulfonic acid, etc., into the reaction system. The acid may be added in an amount of 0.5 to 20 wt%, preferably 2 to 10 wt%.

The reaction may preferably be carried out at a temperature of 50° to 150° C. and it usually is carried out, at the boiling point of the alcohol or the solvent while refluxing the reaction mixture. Further, while the reaction usually is conducted under ordinary pressure it may also be carried out under a pressure of up to around 20 atm.

Next, Examples of this invention will be described below. The reaction vessel used in each of the Examples is a 50 ml flask equipped with a thermometer and a reflux condenser. The yield of the formed ester of cyanoacetic acid in each of the Examples has been calculated based on the starting material, cyanoacetaldehyde acetal.

EXAMPLE 1

In a flask, there were placed 10.3 mmoles of cyanoacetaldehyde di-n-butyl acetal, 20 mmoles of hydroxylamine hydrochloride and 20 ml of ethanol and the mixture was heated under reflux for 7 hrs.

As a result of gas-chromatographic analysis of the reaction mixture, it was found that 6.2 mmoles of ethyl cyanoacetate was produced. (yield: 60%)

EXAMPLE 2

In a flask, there were placed 5.1 mmoles of cyanoacetaldehyde di-n-butyl acetal, 10 mmoles of hydroxylamine hydrochloride, 20 ml of ethanol and 1.25 ml of conc. hydrochloric acid and the mixture was heated under reflux for 1.5 hrs.

As a result of gas-chromatographic analysis of the reaction mixture, it was found that 3.8 mmoles of ethyl cyanoacetate was produced. (yield: 75%)

EXAMPLES 3 TO 5

In a flask, there were placed 5.1 mmoles of cyanoacetaldehyde di-n-butyl acetal, 5.0 mmoles of hydroxylamine sulfate, 20 ml of ethanol and a predetermined amount of 98 wt% sulfuric acid and the resulting mixture was heated under reflux for a predetermined period of time.

The results are shown in Table 1.

TABLE 1

| Example No. | Used amount of 98 wt % sulfuric acid (ml) | Time of heating under reflux (hr.) | Produced ethyl cyanoacetate Amount (mmole) | Yield (%) |
| --- | --- | --- | --- | --- |
| 3 | 0.5 | 4.5 | 3.1 | 61 |
| 4 | 0.5 | 15 | 4.4 | 86 |
| 5 | 1.0 | 3 | 4.1 | 80 |

EXAMPLES 6 TO 9

In a flask, there were placed 5.1 mmoles of cyanoacetaldehyde di-n-butyl acetal, 5.5 g of an aqueous solution of hydroxyamine sulfate having a composition shown in Table 2, which had been obtained in the process for lactam snthesis, and a predetermined amount of one of various alcohols, and the resulting mixture was heated under reflux for a predetermined period of time.

The results are shown in Table 3.

TABLE 2

| Compositions of aqueous solutions of hydroxylamine sulfate | |
| --- | --- |
| Compound | Concentration (wt %) |
| (NH$_2$OH)$_2$.H$_2$SO$_4$ | 15 |
| (NH$_4$)$_2$SO$_4$ | 30 |
| H$_2$SO$_4$ | 12 |
| NH$_4$NO$_3$ | 1 |
| NH$_2$SO$_3$H | 1 |
| H$_2$O | 41 |

TABLE 3

| Example No. | Used alcohol (used amount, ml) | Time of heating under reflux (hr.) | Produced ester of cyanoacetic acid (yield, %) |
| --- | --- | --- | --- |
| 6 | methanol (4) | 13 | methyl cyanoacetate (67) |
| 7 | ethanol (4) | 7 | ethyl cyanoacetate (55) |
| 8 | n-butanol (4) | 13 | n-butyl cyanoacetate (59) |
| 9 | n-butanol (20) | 13 | n-butyl cyanoacetate (69) |

EXAMPLE 10

The reaction was carried out in the same manner as in Example 2 except that 5.5 mmoles of 2-cyanomethyl-1,3-dioxorane was substituted for the cyanoacetaldehyde di-n-butyl acetal.

As the result, it was found that 4.4 mmoles of ethyl cyanoacetate was produced. (yield: 80%)

EXAMPLE 11

The reaction was carried out in the same manner as in Example 4 except that 5.5 mmoles of α-ethyl-α-cyanoacetaldehyde diethyl acetal was used in place of the cyanoacetaldehyde di-n-butyl acetal.

As the result, it was found that 4.5 mmoles of ethyl α-ethyl-α-cyanoacetate was produced. (yield: 82%)

EXAMPLE 12

In a flask, there were placed 5.2 mmoles of α-cyano-α-phenyl-acetaldehyde dimethyl acetal, 10.4 mmoles of hydroxylamine hydrochloride, 20 ml of ethanol and 0.5 ml of conc. hydrochloric acid and the resulting mixture was heated under reflux for 15 hrs.

As a result of gas-chromatographic analysis of the reaction mixture, it was found that 4.1 mmoles of ethyl α-phenyl-α-cyanoacetate was produced. (yield: 79%)

We claim:

1. A process for preparing an ester of cyanoacetic acid with an alcohol selected from the group consisting of an aliphatic alcohol, a substituted aliphatic alcohol having a nitro group or a halogen atom substituent, an alicyclic alcohol and a substituted alicyclic alcohol having a nitro group or a halogen atom substituent which comprises reacting
(i) a cyanoacetaldehyde acetal represented by the general formula

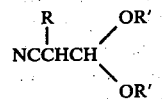

wherein R is a hydrogen atom, an alkyl group, a substituted alkyl group having a nitro group or a halogen atom substituent, a cycloaklyl group, a substituted cycloalkyl group having a nitro group or a halogen atom substituent, a phenyl group, a substituted phenyl group having a nitro group or a halogen atom substituent, an aralkyl group, and a substituted aralkyl group having a nitro group or a halogen atom, and R' is an alkyl group, a substituted alkyl group having a nitro group or a halogen atom substituent, a cycloalkyl group, a substituted cycloalkyl group having a nitro group or a halogen atom substituent, a phenyl group, a substituted phenyl group having a nitro group or a halogen atom substituent, an aralkyl group, a substituted aralkyl group having a nitro group or a halogen atom substituent, and the two R' groups can be linked to form a bridging alkylene group;
(ii) hydroxylamine; and
(iii) an alcohol selected from the group consisting of an aliphatic alcohol, a substituted aliphatic alcohol having a nitro group or a halogen atom substituent, an alicyclic alcohol and a substituted alicyclic alcohol having a nitro group or a halogen atom substituent,
with each other at a temperature of 50° to 150° C., the amount of said hydroxylamine being within the range of 0.1 to 10 moles per one mole of said cyanoacetaldehyde acetal, to form said ester of cyanoacetic acid.

2. The process as claimed in claim 1, wherein the amount of the hydroxylamine is within the range of 1 to 5 moles per one mole of the cyanoacetaldehyde acetal.

3. The process as claimed in claim 1, wherein the alcohol is used in large excess of the cyanoacetaldehyde acetal and the hydroxylamine.

4. The process as claimed in claim 1, wherein an acid is added to the reaction system in an amount of 0.5 to 20 wt% based on the reaction mixture.

5. The process as claimed in claim 4, wherein the amount of the acid is within the range of 2 to 10 wt% based on the reaction mixture.

6. The process as claimed in claim 2, wherein the alcohol is used in large excess of the cyanoacetaldehyde acetal and the hydroxylamine.

7. The process as claimed in claim 2, wherein an acid is added to the reaction system in an amount of 2 to 10 wt% based on the reaction mixture.

8. The process as claimed in claim 3, wherein an acid is added to the reaction system in an amount of 2 to 10 wt% based on the reaction mixture.

9. The process as claimed in claim 6, wherein an acid is added to the reaction system in an amount of 2 to 10 wt% based on the reaction mixture.

* * * * *